United States Patent [19]

Dunigan et al.

[11] 4,001,287

[45] Jan. 4, 1977

[54] REACTION PRODUCT OF NORMAL LEAD BETA RESORCYLATE AND MONOBASIC CUPRIC SALICYLATE

[75] Inventors: Thomas E. Dunigan, Oak Ridge; George C. Sisco, Budd Lake, both of N.J.

[73] Assignee: The United States of America as represented by the Secretary of the Army, Washington, D.C.

[22] Filed: Feb. 18, 1972

[21] Appl. No.: 226,580

Related U.S. Application Data

[62] Division of Ser. No. 78,954, Oct. 7, 1970.

[52] U.S. Cl. .............................. 260/435 R; 149/98
[51] Int. Cl.² ......................................... C07F 7/24
[58] Field of Search ................ 260/435 R, 438.1

[56] References Cited

UNITED STATES PATENTS 3,138,499   7/1964   Camp et al. ..................... 149/98 X

*Primary Examiner*—Leland A. Sebastian
*Attorney, Agent, or Firm*—Nathan Edelberg; A. Victor Erkkila

[57] ABSTRACT

An organo-metallic ballistic modifier produced as an evaporation residue by the reaction of normal lead beta resorcylate and monobasic cupric salicylate in an aqueous solution of water or alcohol at an elevated temperature (180° F - 220° F). The modifier allows the use of a solvent or solvent/solventless process in the production of double base propellants exhibiting a mesa burning rate.

1 Claim, 8 Drawing Figures

REACTION PRODUCT OF NORMAL LEAD BETA RESORCYLATE AND MONOBASIC CUPRIC SALICYLATE

The invention described herein may be manufactured, used and licensed by or for the government for governmental purposes without the payment to us of any royalty thereon.

This is a Divisional Application of application Ser. No. 78,954 filed Oct. 7, 1970.

BACKGROUND OF THE INVENTION

This invention relates to a ballistic modifier for use in a double base propellant mixture in which a mesa burning effect is desired. Processes for making double base propellants exhibiting a mesa effect by solvent means incorporating said ballistic modifier are also provided by the invention.

At a given temperature, the burning rate of a propellant is in direct relationship to the pressure to which it is exposed. Mathematically the relationship is expressed as: $r = cp^n$ where $r$ is the burning rate, $p$ is the pressure and $c$ and $n$ are constants determined by the type of propellant used.

Where $n$ equals zero or some negative value the burning rate will exhibit a plateau or mesa effect. Propellants exhibiting either a plateau or mesa effect give a constant or decreasing burning rate and as a result a steady thrust. Thus vehicles using such propellants exhibit flatter and more ascertainable trajectories.

In the past propellants with a desired mesa burning rate were produced by the mixture of a nitrocellulose-nitroglycerin double base propellants with lead and copper salts of aromatic acids and various plasticizers and stabilizers. The mixture was accomplished by a solventless process in which the water-wet nitrocellulose and a mixture of nitroglycerin in a plasticizer was added and was thoroughly mixed to insure uniformity.

The mixture was filtered or centrifuged to remove most of the water and the resulting paste was aged for several days at a warm temperature. After aging ballistic modifiers were added to the paste which was blended and then milled to a homogeneous colloid on a heated differential rolling mill. The colloid was even-speed milled to produce carpet rolls which could then be extruded, sized or embossed.

Although acceptable, this type of process required extensive machinery, was not economic, and inherently lacked reproducibility as to ballistic modification thus giving rise to varying mesa values in each particular batch of propellant.

Secondly, the process while producing a propellant with good ballistics, that is, mesa burning rate, did not produce a propellant with desired physical strength.

The present invention is an organo-metallic salt complex suitable for use as a ballistic modifier and which allows the production of propellants by a solvent or a solvent/solventless process.

It is an object of this invention to provide an improved ballistic modifier.

A further object of this invention is the preparation of the organometallic ballistic modifier.

A still further object of this invention is to provide a solvent process solvent and a solvent/solventless process which produces a propellant with both desirable mesa effects and increased physical strength incorporating such modifier.

Yet another object of this invention is to provide a solvent process and a solvent/solventless process for producing mesa type propellants which is more efficient and economical than previous solventless type processes.

Yet another object of this invention is to provide a solvent process and a solvent/solventless process for producing mesa type propellants which have a high degree of reproducibility as to a specific mesa burning rate.

Other objects and many of the attendant advantages of this invention will be readily appreciated as the same becomes better understood by reference to the following detailed description.

The present modifier is produced independently of the propellant mix by reacting about equal parts by weight of normal lead beta resorcylate and basic cupric salicylate in a water solution at an elevated temperature. Upon evaporation of the water, a deep green salt complex remains as a residue.

In addition to the aforementioned percentages by weight, the modifier may be produced by about the following weight percentages of the two salts: normal lead beta resorcylate (85–15 percent) and basic cupric salicylate (15–85 percent). Optimum yield of the modifier complex occurs however when the two salts are added in equal parts.

The temperature of the water solution may range from 180° F to 212° F with no appreciable change in yield.

The same modifier complex may be produced by substituting an alcohol solution totally or in part for the water solution.

Alcohols that have been found effective include methanol, ethanol, isopropanol, and tertiary/butyl/alcohol.

The modifier once formed as a residue may be used in a solvent process or a solvent/solventless process for the manufacture of propellants producing propellants exhibiting a mesa burning rate.

The solvent and solvent/solventless processes for the manufacture of propellants consist essentially of forming mixtures of water-wet nitrocellulose and ballistic modifier and nitroglycerin with various stabilizers and plasticizers. The mixtures are then combined, colloided, screened, extruded and dried to produce homogeneous propellant strands.

Stabilizers which have been found effective consist of any compound or mixture of compounds which prevent the decomposition of nitrocellulose while not interfering with the ballistic or structural properties of the propellant. Examples include: diphenylamine, 2 nitrodiphenylamine, ethyl centralite and n-methyl p-nitroaniline.

Examples of plasticizers which may be used to advantage include nitroglycerin, diethylene glycol dinitrate, triethylene glycol dinitrate, dinormal propyl adipate, 1,2,3 butanetriol trinitrate, 1,2,4 butanetriol trinitrate and trimethylolethane.

Other additives may be added to produce certain desired effects for example: candelilla wax as an extrusion lubricant and carbon black as an opacifying agent.

Colloiding mediums which have been found effective consist of any agent capable of colloiding gun cotton. Examples include: acetone, ethyl acetate, methyl ethyl ketone and ethylene glycol monomethyl ether.

By inclusion of the step of over-colloiding in the propellant's manufacture, that is, the addition of one of the colloiding solvents in excess, mesa ballistic characteristics are enhanced.

By use of these processes in the propellant's manufacture, the desired mesa effect is achieved and good physical characteristics, e.g., increased strength are imparted to the propellant.

Further, by use of solvent and solvent/solventless processes, the degree of colloiding during mixing may be rigidly controlled. This, in time, results in a high degree of reproducibility from batch to batch.

With the elimination of several operations inherently found in the solventless process, the cost and time savings would be substantial.

Although it is not intended that the invention be limited thereto, there is set forth herein below for purposes of illustration, examples of how the ballistic modifier may be produced and solvent and solvent/solventless processes incorporating such ballistic modifier producing propellants which exhibit a mesa burning rate while retaining superior physical strength.

EXAMPLE I 800 grams of n-lead-B resorcylate and 800 grams of basic cupric salicylate were ground and mixed by hand. The mixture was then wet by the addition of hot water and steam and the resultant slurry mixed in a vertical sigma blade mixer at a temperature of 180° F. After complete mixing the solution was evaporated down to a residue. The residue was pulverized and screened through a U.S. No. 270 sieve. Ethanol and various mixtures of water and ethanol were also used to form the slurried mixtures.

EXAMPLE II 150 grams of n-lead-B resorcylate and 850 grams of basic cupric salicylate were ground and mixed by hand. The mixture was then wet by the addition of hot water and steam and the resultant slurry mixed in a vertical sigma blade mixer at a temperature of 180° F. After complete mixing the solution was evaporated down to a residue. The residue was pulverized and screened through a U.S. No. 270 sieve. Ethanol and various mixtures of water and ethanol were also used to form the slurried mixtures.

EXAMPLE III 150 grams of basic cupric salicylate and 850 grams of n-lead-B resorcylate were ground and mixed by hand. The mixture was then wet by the addition of hot water and steam and the resultant slurry mixed in a vertical sigma blade mixer at a temperature of 180° F. After complete mixing the solution was evaporated down to a residue. The residue was pulverized and screened through a U.S. No. 270 sieve. Ethanol and various mixtures of water and ethanol were also used to form the slurried mixtures.

| % By Weight | Example IV<br>Propellant Composition |
| --- | --- |
| 49.1 | Nitrocellulose |
| 40.6 | Nitroglycerin |
| 3.3 | Dinormal-propyl adipate |
| 2.0 | 2-nitro-diphenylamine |
| 5.0 | Ballistic Modifier |

10 percent water-wet nitrocellulose, ballistic modifier and 2-nitro diphenylamine were mixed in a sigma blade mixer at ambient temperatures for about 30 minutes.

Dinormal propyl adipate and nitroglycerin were added to the mixture and an excess of acetone added to the mixture to induce colloidization.

A flow of gas is passed over the mixture in the mixer to remove the volatile solvent. The colloided mixture becomes a rubbery mass which, with the removal of more and more solvent, then crumbles into small particles.

The particles are then screened through No. 12, 24 and 36 mesh screens at various gage pressures [300–900–450 (psig).]

The screened particles are then extruded through a solvent press with a 0.117 in die and wrapped on drying racks. It is dried at ambient temperature for 21 days.

| % By Weight | Example V<br>Propellant Composition |
| --- | --- |
| 49.1 | Nitrocellulose |
| 40.6 | Nitroglycerin |
| 3.3 | Dinormal-propyl adipate |
| 2.0 | 2-nitro-diphenylamine |
| 5.0 | Ballistic Modifier |

10 percent water-wet nitrocellulose, ballistic modifier and 2-nitro diphenylamine were mixed in a sigma blade mixer at ambient temperatures for about 30 minutes.

Dinormal propyl adipate and nitroglycerin were added to the mixture and an excess of acetone added to the mixture to induce colloidization.

A flow of gas is passed over the mixture in the mixer to remove the volatile solvent. The colloided mixture becomes a rubber mass which, with the removal of more and more solvent, then crumbles into small particles.

The particles are then screened through No. 12, 24 and 36 mesh screens at various gage pressures [300–900–450 (psig).]

The screened particles are then extruded through a solvent press with a 0.117 in die and cut at a 0.120 in interval.

The extruded material known as press feed is cured for 7 days at ambient temperature and oven dried at 50° C for 10 days.

The dried press feed is pressed again at 160° F under varying pressures (300–900 psig) to extrude the propellant to the desired dimensions.

The advantages of the invention will be better understood from the description which follows taken in connection with the drawings which form a part of this specification, the figures representing graphs of the pressure-burning rate relationships for various propellants tested.

Standard procedures were used to determine burning rates which were carried out in a Crawford Strand Burning Rate Apparatus.

FIG. 1 depicts the mesa curve obtained when a ballistic modifier with the composition outlined in Example I is added to the propellant mixture.

FIG. 2 depicts the plateau curve obtained when a ballistic modifier with the composition outlined in Example III is added to the propellant mixture.

FIG. 3 illustrates the plateau curve obtained when a ballistic modifier with the composition outlined in Example II is added to the propellant mixture.

FIG. 5 depicts the mesa curve obtained when a ballistic modifier with the composition outlined in Example I is added to the propellant mixture.

FIG. 6 depicts the plateau curve obtained when a ballistic modifier with the composition outlined in Example III is added to the propellant mixture.

Figure 1:
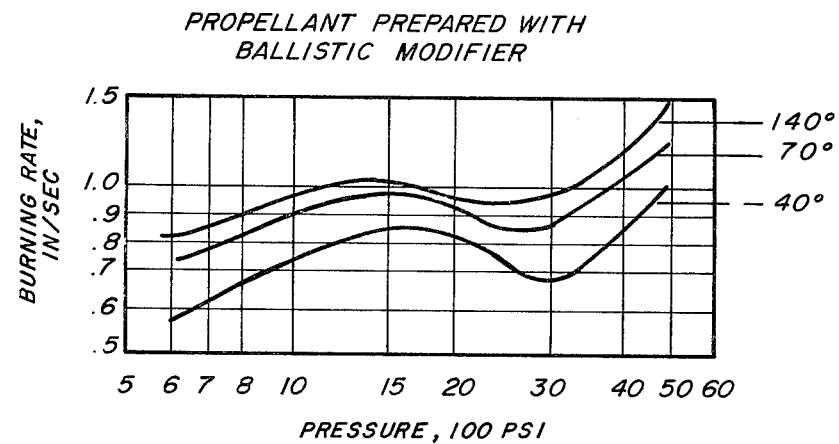
FIGS. 1–3 represent pressure-burning rate graphs of propellants with the percentage composition and produced by the solvent means outlined in Example IV; more specifically.
Figure 2:
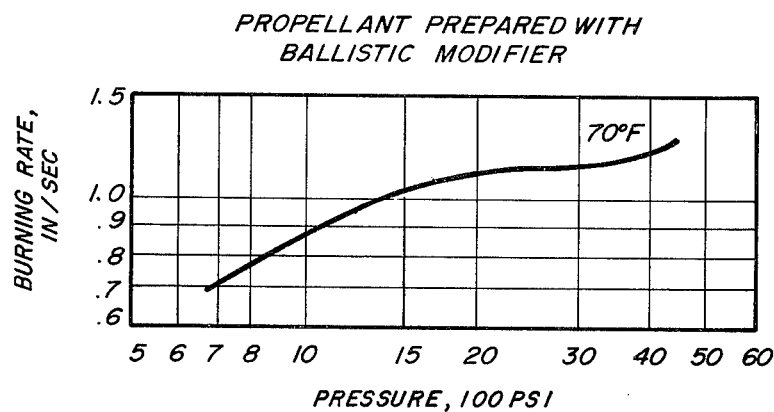
Figure 3:
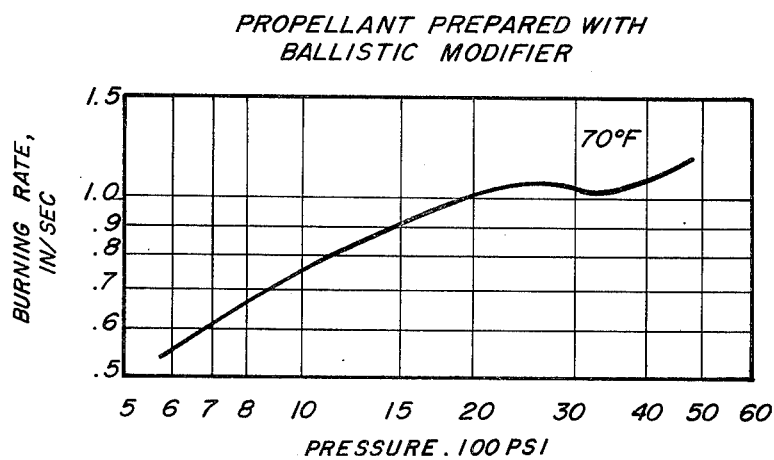
Figure 4:
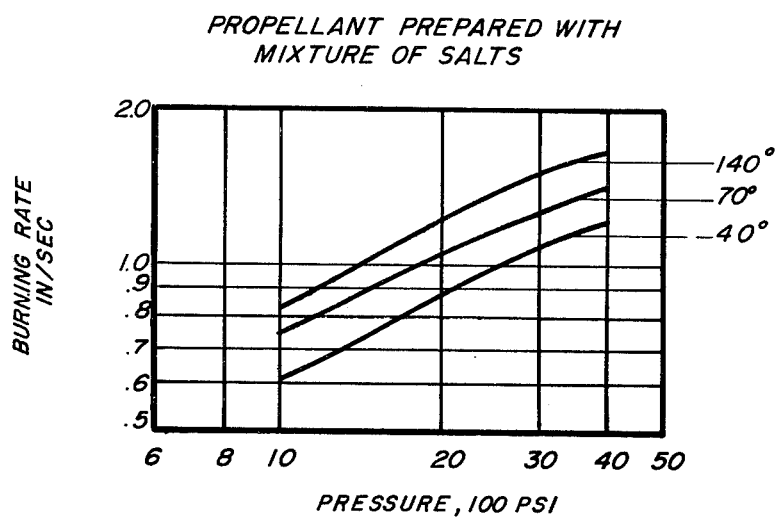
FIG. 4 represents a propellant mixture as depicted in Example IV except that a mechanical mixture of equal weights of normal lead beta resorcylate and monobasic cupric salicylate is substituted for the ballistic modifier. Neither mesa not plateau curves are achieved through the use of this mixture.
Figure 5:
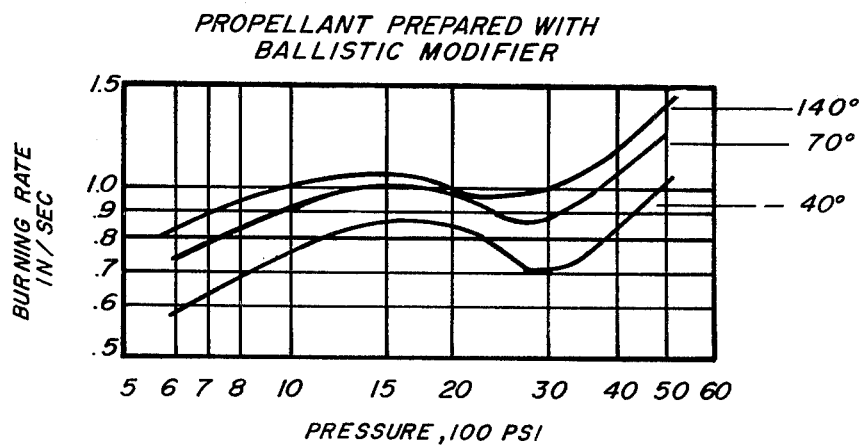
FIGS. 5–7 represent pressure-burning rate graphs of propellants with the percentage composition and produced by the solvent/solventless means outlined in Example V; more specifically.
Figure 6:
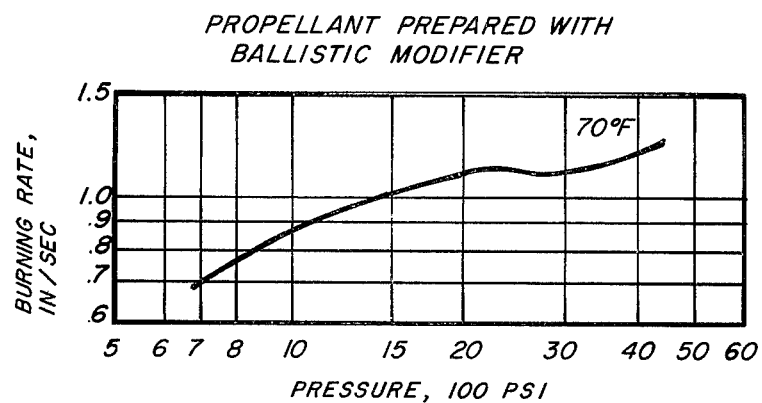
Figure 7:
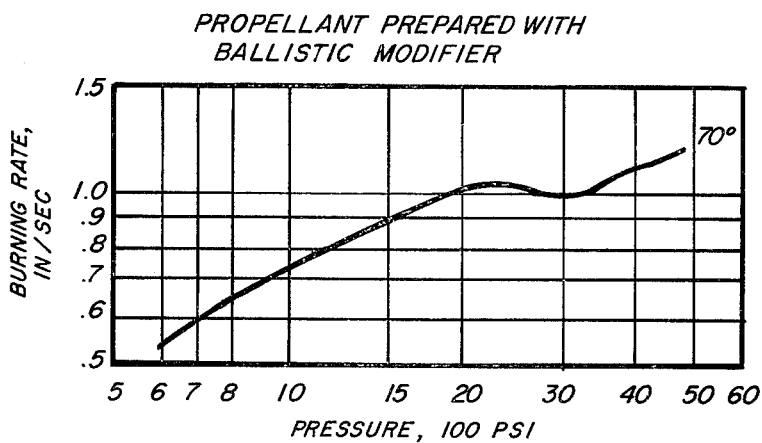

FIG. 7 represnts the plateau curve obtained when a ballistic modifier with the composition outlined in Example II is added to the propellant mixture.

Figure 8:
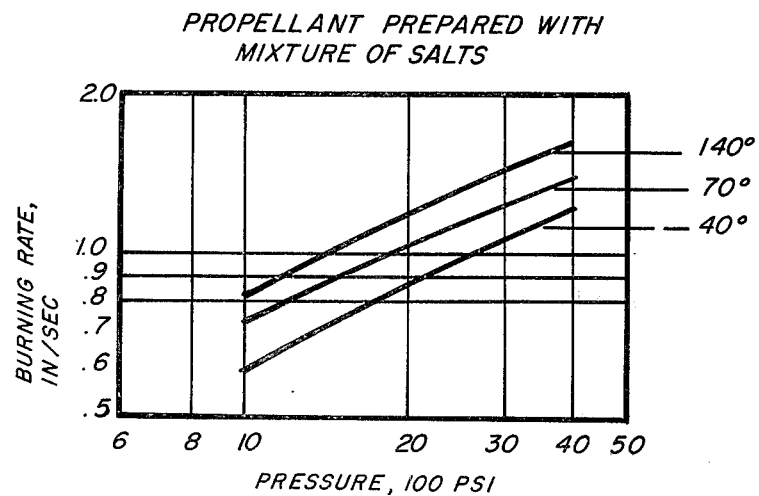

FIG. 8 represents a propellant mixture as depicted in Example V except that a mechanical mixture of equal weights of normal lead beta resorcylate and monobasic cupric salicylate is substituted for the ballistic modifier. Neither mesa nor plateau curves are achieved through the use of this mixture.

As is demonstrated by the graphs optimum mesa modification occurs when the ballistic modifier consists of equal parts of the organo-metallic salts. The first plataeu modification occurs when the ballistic modifier consists of 15–85 and 85–15 percent by weight, of the organo-metallic salts. Thereafter no modification takes place and straight line graphs are obtained.

Differential Thermal analysis of the ballistic modifier and mechanical mixtures of the organo-metallic salts tend to confirm the above results.

Thus, through the practice of our invention, mesa and plateau burning rates may be obtained in solvent and solvent/solventless processes inherently less costly, requiring less machinery, and providing better reproducibility in burning rate than previous solventless processes.

We wish it to be understood that we do not desire to be limited to the exact processes shown and described for obvious modification will occur to a person skilled in that art.

We claim:

1. An organo-metallic complex consisting essentially of the residue product of the interacting of 15–85% by weight of normal lead beta resorcylate and 85–15% by weight of monobasic cupric salicylate in a solvent medium of the group consisting of water and an alcohol and mixtures thereof at an elevated temperature of at least about 180° F.

* * * * *